United States Patent
Schoelling et al.

[11] Patent Number: 5,958,321
[45] Date of Patent: Sep. 28, 1999

[54] PROCESS AND APPARATUS FOR PRODUCING A TAMPON APPLICATOR FOR FEMININE HYGIENE

[76] Inventors: Hans-Werner Schoelling, Dohlenweg 11, D58252, Ennepetal, Germany; Theodor Schoettli, Schlattinger Buck, CH-8253, Diessenhofen, Switzerland

[21] Appl. No.: 08/931,154

[22] Filed: Sep. 16, 1997

[30] Foreign Application Priority Data

Sep. 17, 1996 [DE] Germany .......................... 196 37 932

[51] Int. Cl.⁶ .............................. A61F 13/32; B29C 45/36
[52] U.S. Cl. ...................... 264/318; 264/334; 264/328.8; 425/556; 425/577; 425/438; 425/DIG. 58
[58] Field of Search ............................... 264/328.8, 238, 264/318, 328.1, 334; 425/553, 554, 556, 577, 438, 441, 64, 145, DIG. 58

[56] References Cited

U.S. PATENT DOCUMENTS

| | | |
|---|---|---|
| 3,124,134 | 3/1964 | Gardner . |
| 3,341,897 | 9/1967 | Susuki et al. ............................. 425/577 |
| 3,402,713 | 9/1968 | Senkowski et al. ..................... 264/318 |
| 3,559,249 | 2/1971 | Patton, Jr. ................................ 425/577 |
| 3,843,088 | 10/1974 | McLoughlin et al. ................... 425/577 |
| 4,479,791 | 10/1984 | Sprague . |
| 5,366,683 | 11/1994 | Cibin ....................................... 264/238 |
| 5,433,912 | 7/1995 | Schulz et al. ........................ 264/297.2 |
| 5,453,085 | 9/1995 | Schoelling . |
| 5,512,228 | 4/1996 | Adams et al. ........................... 264/238 |
| 5,533,966 | 7/1996 | Schoelling . |
| 5,624,694 | 4/1997 | Delaby et al. ........................... 425/577 |
| 5,690,884 | 11/1997 | Cerny ................................... 264/328.1 |

FOREIGN PATENT DOCUMENTS

90/11747 10/1990 WIPO .

*Primary Examiner*—Jill L. Heitbrink

[57] ABSTRACT

A moldable material is injected substantially simultaneously into a mold cavity for the outer sleeve formed between an outer sleeve mold and an outer sleeve core in an injection unit and into a mold cavity for the inner sleeve formed between an inner sleeve mold and an inner sleeve core in a clamping unit of a mold. These mold cavities are connected by at least one relatively thin runner to form at least one predetermined breaking point between the rear end of the outer sleeve and the front end of the inner sleeve of a one-part applicator molding. The invention also relates to an apparatus for producing the tampon applicator according to, but not restricted to, the process as described above.

21 Claims, 9 Drawing Sheets

PROCESS AND APPARATUS FOR PRODUCING A TAMPON APPLICATOR FOR FEMININE HYGIENE

BACKGROUND OF THE INVENTION

The invention relates to a process and an apparatus for producing a tampon applicator for feminine hygiene from moldable material, which applicator comprises an approximately cylindrical outer sleeve and an approximately cylindrical inner sleeve, the outside diameter of the inner sleeve being made smaller than the inside diameter of the outer sleeve, in which the inner sleeve can be arranged telescopically displaceably. The process concerns the injection of moldable material into a mold cavity with a core for the outer sleeve and into a mold cavity with a core for the inner sleeve of the tampon applicator.

Over the years there have been many developments in molding plastic tampon applicators. Many are formed as individual, separate pieces, such as an outer sleeve and an inner sleeve or plunger, that are combined during the assembly of the tampon and applicator. An example of this type may be seen in Sprague, U.S. Pat. No. 4,479,791. Unfortunately, this requires separate handling of the applicator components and their careful orientation during assembly to ensure that the parts line up adequately. This is especially true of applicators that have some interlocking of the components, such as compact tampon applicators. An example of this type may be seen in McNeil-PPC, Inc., WO 90/11747. This compact tampon applicator has a retaining tang or tampon catch projecting from the outer sleeve of the applicator, through a slot in the inner sleeve to bear against the rear of the tampon while the applicator is being prepared for expulsion of the tampon.

Attempts have been made to form at least a portion of both the outer sleeve and inner sleeve at the same time. One example of this is Gardner, U.S. Pat. No. 3,124,134, which illustrates an outer tube and inner tube which are initially molded as an integral, one-piece construction which is separated before packing the tampon into the applicator. Another example, Schoelling, U.S. Pat. Nos. 5,453,085 and 5,533,966, allows the two components to be maintained together until use. These devices include an outer sleeve for containing a tampon, a hollow grip piece inserted in the rear end of the outer sleeve, and an inner plunger. The plunger is originally connected to the grip piece by mean of at least one predetermined breaking point to eliminate the possibilities of the plunger from being separated from the holder and outer sleeve during handling prior to use. The predetermined breaking point is then fractured just prior to use to allow the plunger to slide axially within the holder to expel the tampon from the outer sleeve.

SUMMARY OF THE INVENTION

The invention is based on the object of significantly simplifying the process and the apparatus for producing a tampon applicator from moldable material and making them more cost-effective, as well as combining them if need be with an assembly of the tampon applicator having an outer sleeve and an inner sleeve.

To achieve this object, the invention relates to a process in which a moldable material is injected substantially simultaneously into a mold cavity for the outer sleeve formed between an outer sleeve mold and an outer sleeve core in an injection unit and into a mold cavity for the inner sleeve formed between an inner sleeve mold and an inner sleeve core of a clamping unit of a mold. These mold cavities are connected by at least one relatively thin runner to form at least one predetermined breaking point between the rear end of the outer sleeve and the front end of the inner sleeve of a one-part applicator molding. The one-part applicator molding is solidified in the mold cavities, and the outer sleeve mold is removed. The outer sleeve core may be coaxially withdrawn through a front opening of the outer sleeve of the one-part applicator molding, and the resulting the one-part applicator molding may be ejected from the inner sleeve mold cavity.

The process according to the invention offers advantages for the production of a tampon applicator whose outer sleeve and inner sleeve are respectively provided with lips on the front end. This process allows these lips to be formed simultaneously onto the front ends of the outer sleeve and of the inner sleeve when the one-part applicator molding is being produced. Similarly, this process permits a tampon catch to be molded on the inner side of the outer sleeve proximate its rear end and an axial guide slot to be formed in the wall of the inner sleeve of the one-part applicator molding during the production of the same. As a result, the inner sleeve is secured in the outer sleeve against loss and is displaceable only to a limited extent within the outer sleeve. In addition, with this known design there can be created a more compact form of the tampon applicator, in which the tampon is arranged within the inner sleeve, which, in turn, is placed into the outer sleeve.

The invention also relates to an apparatus for producing the tampon applicator. The apparatus has an injection unit and a clamping unit. In the closed state, these form an outer sleeve mold cavity having an outer sleeve core arranged in the injection unit and an inner sleeve mold cavity having an inner sleeve core in the clamping unit. Again in the closed state, at least one thin runner is provided in the region of its parting plane for producing at least one predetermined breaking point between the rear end of the outer sleeve and the front end of the inner sleeve of the one-part applicator molding.

Further developments of the invention concern the axial mobility of the outer sleeve core within the injection unit, so that the core bearing the outer sleeve of the one-part applicator molding can be moved along synchronously with and bearing against the inner sleeve core in the clamping unit on a first opening stroke of the clamping unit. As a result, the outer sleeve molded in one part with the inner sleeve lies free in the interspace between injection unit and opened clamping unit of the mold. Subsequently, the outer sleeve core can be moved back into the injection unit. A stripping sleeve, movable axially back and forth in the clamping unit on the inner sleeve core, can subsequently be moved in the ejecting direction toward the rear end of the inner sleeve to strip the inner sleeve from its core in the clamping unit. Thus, the one-part applicator molding can be ejected from the apparatus and can be passed on for further treatment.

In addition, a handling device can be used to substantially immobilize the outer sleeve while the stripping sleeve in the clamping unit can strip off the inner sleeve and push it into the outer sleeve. This destroys the at least one predetermined breaking point between the inner sleeve and the outer sleeve and pushes the inner sleeve into a locked position in the outer sleeve by engaging at least one catching hook, formed on the outer sleeve by the destruction of the predetermined breaking point, with a catching element formed on the inner sleeve.

DETAILED DESCRIPTION OF THE PREFERRED EMBODIMENT

Figure 1:
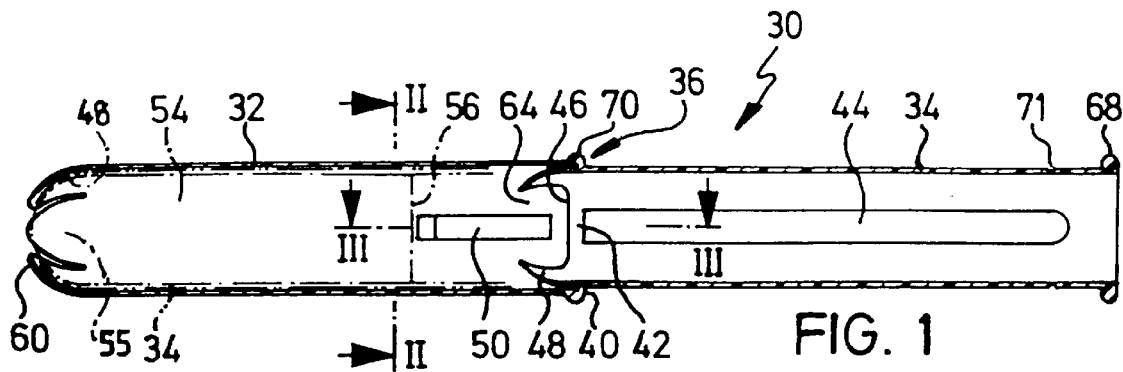
FIG. 1 shows a first embodiment of a one-part applicator molding, produced completely from moldable material, in a central longitudinal section.

In FIGS. 1 to 4 there is shown a one-part applicator molding 30 for a tampon applicator for feminine hygiene of moldable material. If desired, the applicator molding 30 may be produced from a single moldable material or else from two moldable materials of different properties, which are, for example, particularly suitable or desired on the one hand for the outer sleeve and on the other hand for the inner sleeve of the tampon applicator. Preferably, the moldable material is a biodegradable plastic, such as polyvinyl alcohol or other injection-moldable biodegradable plastics. However, other injection-moldable plastics, such as polyolefins, polyesters, and the like, may also be used.

The applicator molding 30 has a substantially cylindrical outer sleeve 32 and a substantially cylindrical inner sleeve 34 with an outside diameter which is smaller than the inside diameter of the outer sleeve 32. The outer sleeve 32 and the inner sleeve 34 are connected to each other by at least one predetermined breaking point 36, so that the outer sleeve 32 and the inner sleeve 34 can be produced as the one-part applicator molding 30 in only one mold of an injection-molding machine, as explained further below. The predetermined breaking point 36 is provided in a front cross sectional region of the inner sleeve 34, which is located in front of a front end 42 of a guide slot 44 closed at both ends and at a lip root 46 of flexible lips 48 of the inner sleeve 34 which are convex, taper toward the front end, are for example spherical-segmental and are resilient.

The at least one predetermined breaking point 36 comprises a thin skin 38 (FIG. 3), which may extend over as much as 360° of the applicator circumference and connects a rear end face 40 of the outer sleeve 32, shown in FIG. 1, to the outer side of the front end of the cylindrical part of the inner sleeve 34. However, it is preferred that the predetermined breaking point 36 is provided along mutually separate circumferential sections of the applicator molding 30, in each case in the form of the thin, web-shaped or spot-shaped skin 38.

Figure 2:
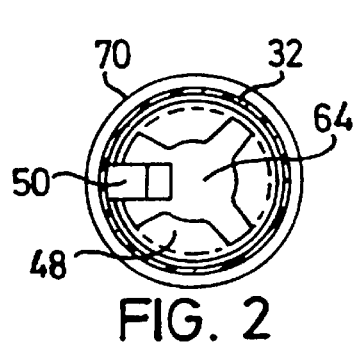
FIG. 2 shows a cross section II—II according to FIG. 1.
Figure 4:
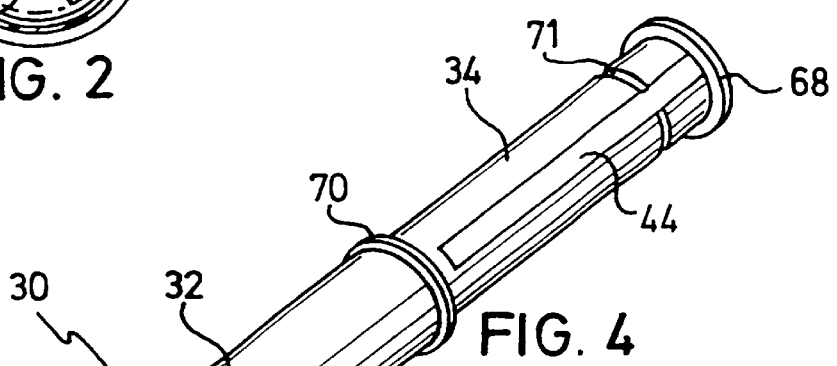
FIG. 4 shows the first embodiment of the one-part applicator molding in FIGS. 1 to 3 in a diagrammatic view.

According to FIG. 1, the outer sleeve 32 is also provided at the front end with six flexible, forward-tapered and respectively convex lips 60 which form a substantially hemispherical closure. The lips 60, 48 of the outer sleeve 32 and of the inner sleeve 34 are rounded off at their edges and free, front ends. In addition, their ends are preferably bent concentrically toward the central longitudinal axis of the tampon applicator 30 and leaving free a relatively large, central opening 62 and 64, respectively, of the outer sleeve 32 and of the inner sleeve 34 (FIGS. 1, 2 and 4).

Figure 3:
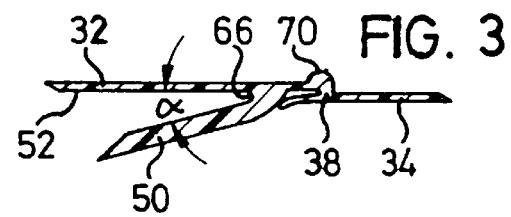
FIG. 3 shows a longitudinal section III—III according to FIG. 1.

According to FIGS. 1 and 3, a tampon catch 50 extends from the outer sleeve 32 at a proximal end 66. The proximal end 66 is preferably separated by a circumferential distance on both sides from three lips 48 of the inner sleeve 34. The tampon catch 50, designed in the manner of a spring clip, is arranged on the inner side of an approximately cylindrical wall 52 of the outer sleeve 32 at an axial distance in front of the rear end face 40 of the outer sleeve 32 and extends in a plane radial to the central longitudinal axis of the outer sleeve 32 and at an acute angle obliquely in the direction of the front end of the outer sleeve 32.

The axial guide slot 44 of the inner sleeve 34 of the one-part applicator molding 30 is aligned with respect to the tampon catch 50 by the predetermined breaking points 36 coaxially, and it is made wider than the tampon catch 50. Consequently, the predetermined breaking points 36 can be destroyed by exerting an axial pressure on the inner sleeve 34 and the inner sleeve 34 can be pushed into the outer sleeve 32 such that the tampon catch 50 is initially bent back flexibly by the lip roots 46 of the inner sleeve 34 against the inner side of the wall 52 of the outer sleeve 32 and thereby prestressed, before it automatically engages, owing to its flexural prestress, into the guide slot 44 radially with snap action and, in the relaxed state, again assumes its original position. This assembly step is generally also assisted by a certain, radial, flexible evasive movement of the front end 42 of the inner sleeve 34 toward the interior of the inner sleeve 34. The length of the tampon catch 50 is made such that a tampon 54 indicated in FIG. 1 in dash-dotted lines bears in an assembly position of the inner sleeve 34 within the outer sleeve 32, shown by dash-dotted lines, by its front, spherical cap-shaped end 55 against the inner side of the lips 60 of the outer sleeve 32 and by its rear end 56 against the free end of the tampon catch 50 and is fixed in its axial position. FIG. 1, alternatively depicts a compact applicator assembly with the inner sleeve 34 nested within the outer sleeve 32, shown by dash-double dotted lines. The spherical cap-shaped end 55 of the tampon 54, in this configuration, bears against the inner side of the lips 48 of the inner sleeve 34.

The inner sleeve 34 in FIGS. 1 to 4 is provided at the rearward end with an annular catching groove 71 at an axial distance in front of an end gripping bead 68. The rear end face 40 of the outer sleeve 32 is formed by a gripping bead 70.

Figure 5:
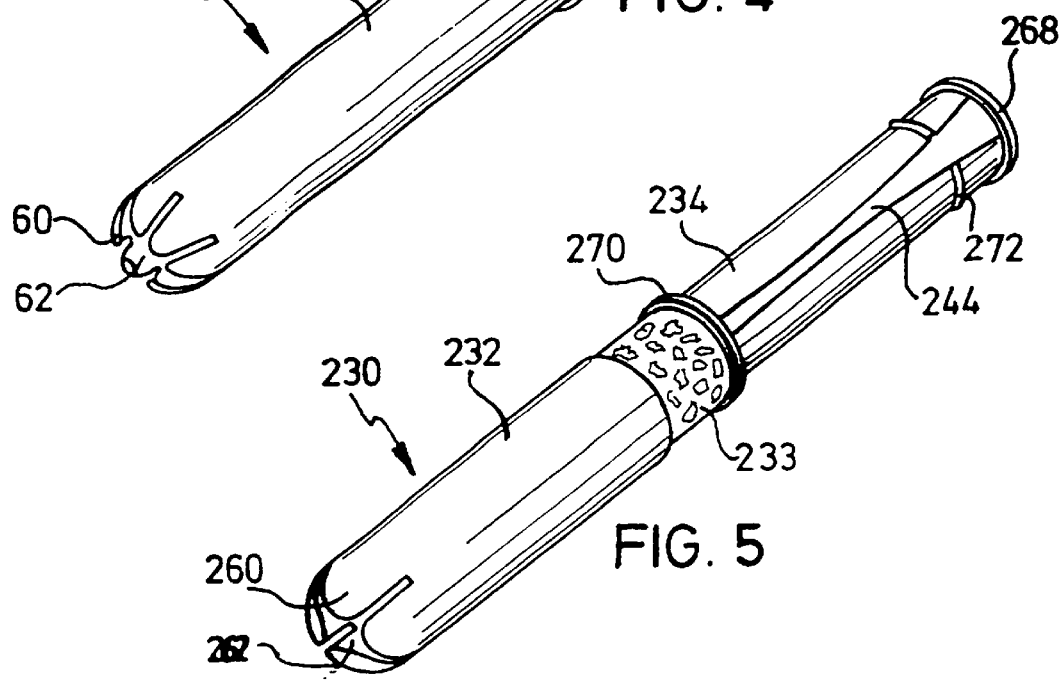
FIG. 5 shows a second embodiment of a one-part applicator molding in a diagrammatic view.

The second embodiment of a one-part applicator molding 230 in FIG. 5 differs from the first embodiment merely in that an outer sleeve 232 has at its front end only four lips 260, which form a front opening 262 for ejecting a tampon. Furthermore, in front of a rear gripping bead 270 of the outer sleeve 232 there is provided a section of length having a roughened gripping surface 233 for better handling of the finished tampon applicator during insertion of a tampon. An inner sleeve 234 differs from the first embodiment essentially by a guide slot 244, which at mid-length is narrower than the tampon catch 50 is wide. Consequently, the inner sleeve 234 is spread and expanded in this region by the tampon catch 50, in order to achieve a reliable guidance of the inner sleeve 234 and an easy pushing out or transferring of the tampon 54 into the outer sleeve 232. The inner sleeve 234 is likewise provided at the rear end with a gripping bead 268, in front of which an annular catching bead 272 is arranged at an axial distance.

Since, upon destruction of the predetermined breaking points 36, remains of the predetermined breaking points 36 remain on the inner side of the wall 52 of the outer sleeve 32 or 232 in the form of attachments (not shown), these attachments may serve as catching hooks or catching ribs which, at the end of the pushing-in movement of the inner sleeve 34 into the outer sleeve 32, engage in the catching groove 71 with a detent action, or slide over the catching bead 272 in a detaining manner, in order as a result to secure the inner sleeve 34 or 234 releasably in its position pushed into the outer sleeve 32 or 232.

Figure 6:
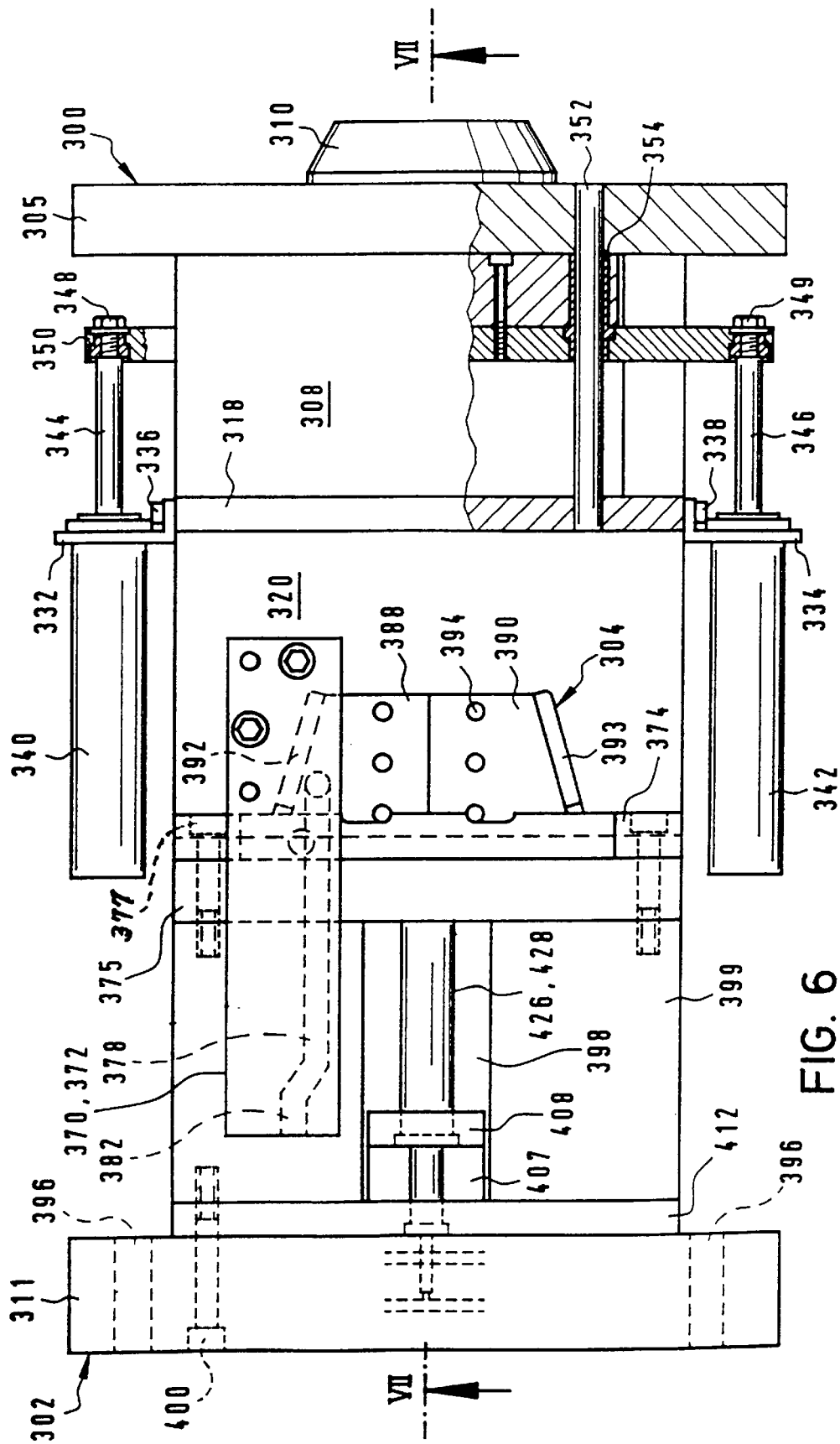
FIG. 6 shows a closed mold of an injection-molding machine for the simultaneous production of both embodiments of the one-part applicator molding according to FIGS. 1 to 5 in plan view.
Figure 7:
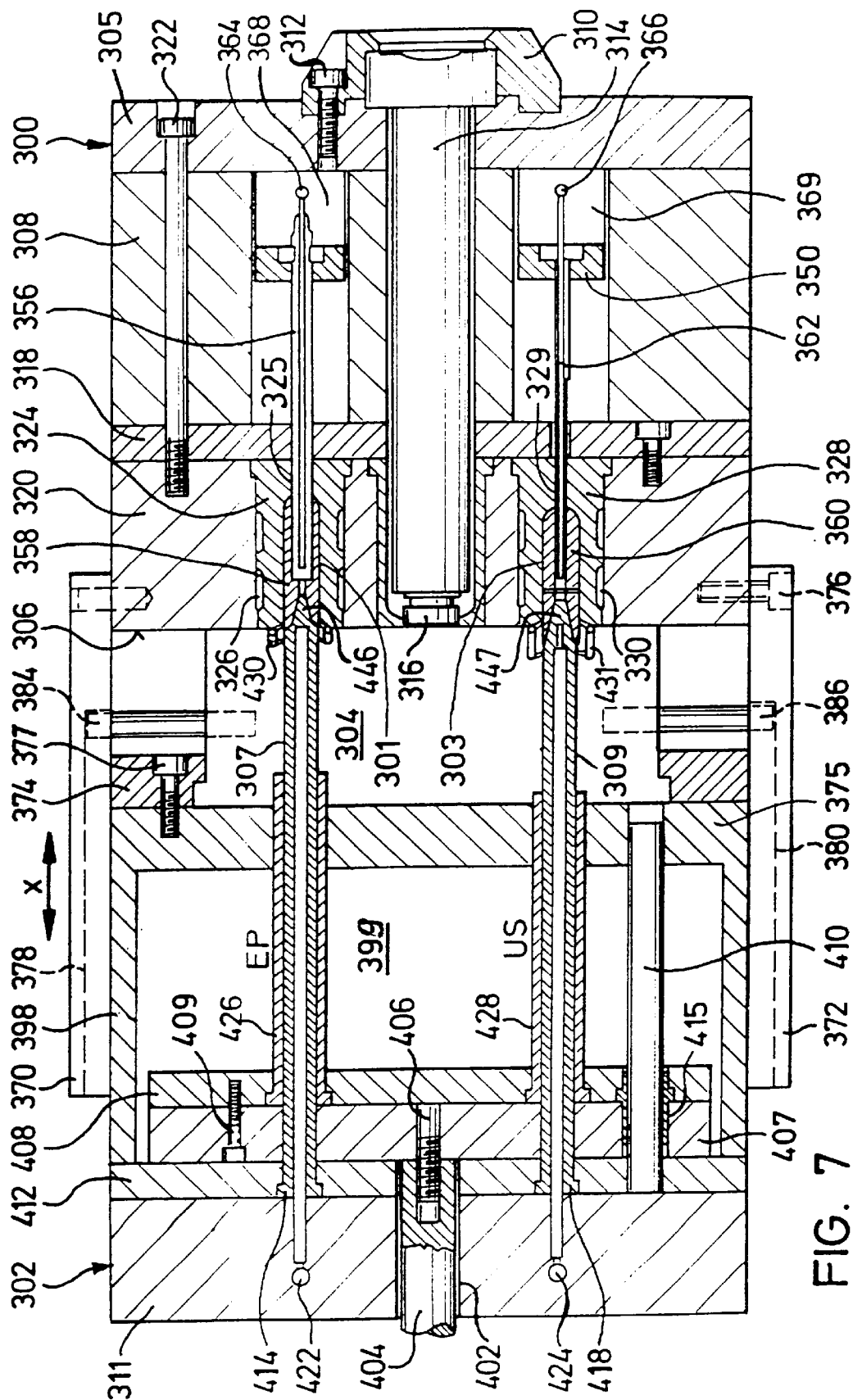
FIG. 7 shows a perpendicular central longitudinal section VII—VII of the closed mold in FIG. 6.

In FIGS. 6 and 7 there is represented an apparatus for the simultaneous production of the first embodiment of the one-part applicator molding 30 in FIGS. 1 to 4 and of the second embodiment of the applicator molding 230 in FIG. 5 in the mold of an injection-molding machine having an injection unit 300 and a clamping unit 302, driven for example oil-hydraulically.

According to FIGS. 6 and 7, the injection unit 300 comprises, inter alia, a platen 305, to which a spacer plate 308, a receiving plate 318 and a support plate 320 for outer-sleeve mold inserts 324, 328 (shown in FIG. 7) with mold cavities 301, 303 for the outer sleeves 32; 232, are firmly braced by means of spacer anchoring screws 322. FIG. 7 shows, furthermore, cooling chambers 326, 330 for cooling fluid at the circumference of the mold inserts 324, 328.

Figure 8:
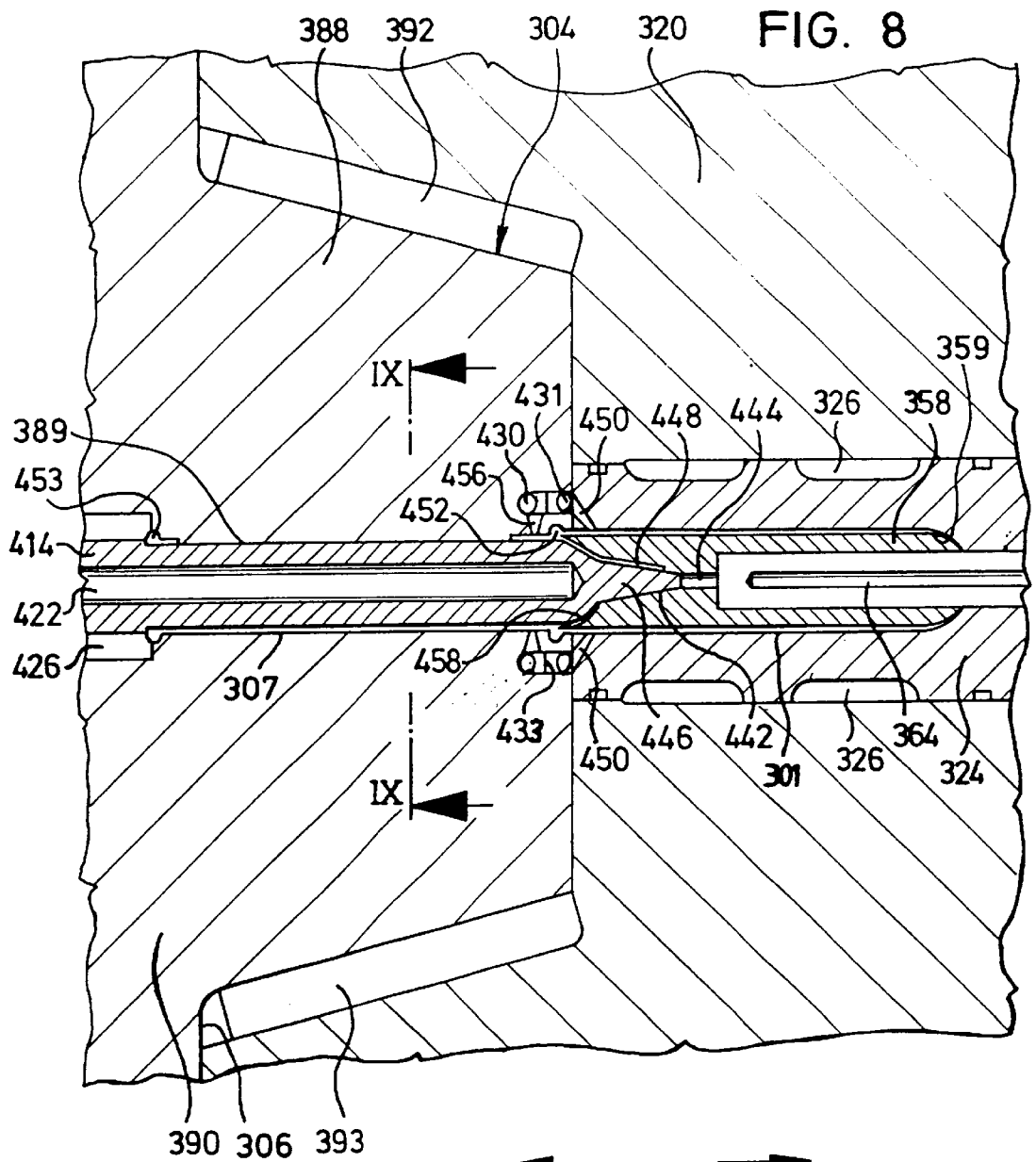
FIG. 8 shows the closed mold for the first embodiment of the one-part applicator molding according to FIGS. 1 to 4 in a central longitudinal section parallel to the plane of the drawing in FIG. 6, on an enlarged scale and in a broken-away representation.

Furthermore, in FIGS. 6, 7 and 8 there can be seen an inner-sleeve mold 304, comprising laterally movable inner-sleeve mold jaws 388, 390, with mold cavities 307, 309 for the inner sleeves 34 or 234 as a component part of the clamping unit 302.

According to FIG. 7, the mold cavity 301 of the mold EP (Europe) contains a core 358 for the outer sleeve 32 of the one-part applicator molding 30 in FIG. 4. Similarly, in the mold cavity 303 of the mold U.S. (United States) there is provided a core 360 for the outer sleeve 232 of the one-part applicator molding 230 in FIG. 5.

Furthermore, in FIGS. 6 and 7, a centering device 310 is fastened by means of screws 312 on the rear side of the platen 305 of the injection unit 300. The centering device 310 is simultaneously the interface with respect to an injection screw (not shown) of the injection-molding machine. Connected to the centering device 310 is an injection tube 314, at the end of which an injection nozzle 316 is arranged.

According to FIG. 6, angle pieces 332, 334 are fastened by screws 336, 338 on opposite narrow sides of the sprue-side receiving plate 318. These angle pieces 332, 334 in each case bear a piston-cylinder unit 340, 342, the piston rods 344, 346 of which are connected by screws 348, 349 to a supporting plate 350. The supporting plate 350 extends parallel to the platen 305 and is moved back and forth by means of the piston-cylinder units 340, 342 with respect to the clamping unit 302 on guide rods 352 by means of guide bushes 354.

According to FIG. 7, fastened on the movable supporting plate 350 are two profile cores 356; 362, which are mounted longitudinally displaceably in the receiving plate 318 for the support plate 320 and extend in each case through a rear longitudinal bore 325; 329 in the mold inserts 324; 328 into the latter. The transverse profile of these profile cores 356; 362 determines the size and contour of the front opening 62; 262 of the outer sleeves 32; 232 in FIGS. 4 and 5. At the front end, the profile cores 356; 362 are provided with their diametrically enlarged cores 358; 360 for the outer sleeves 32; 232, which are arranged in the mold cavities 301 and 303, respectively, of the mold inserts 324; 328 for the outer sleeves 32; 232 of the applicator moldings 30; 230 according to FIGS. 4 and 5.

According to FIG. 8, the outer-sleeve core 358 is provided at its front extreme end, facing away from the clamping unit 302, with a convex end face 359, which is provided with tongue-shaped, spherical-segmental recesses (not shown) for forming the six lips 60 of the outer sleeve 32. It goes without saying that the outer-sleeve core 360 in FIG. 7 likewise has recesses (not shown), corresponding to the four lips 260 of the outer sleeve 232, at its front, rounded-off extreme end, facing away from the clamping unit 302.

According to FIGS. 7, 8, 10 and 11, the profile cores 356, 362 in each case contain axial coolant channels 364, 366, which are led into the outer-sleeve cores 358, 360 and, according to FIG. 7, are connected by in each case a manifold block 368, 369 in the movable supporting plate 350 (FIG. 6) to pressurized coolant sources (not shown).

Figure 10:
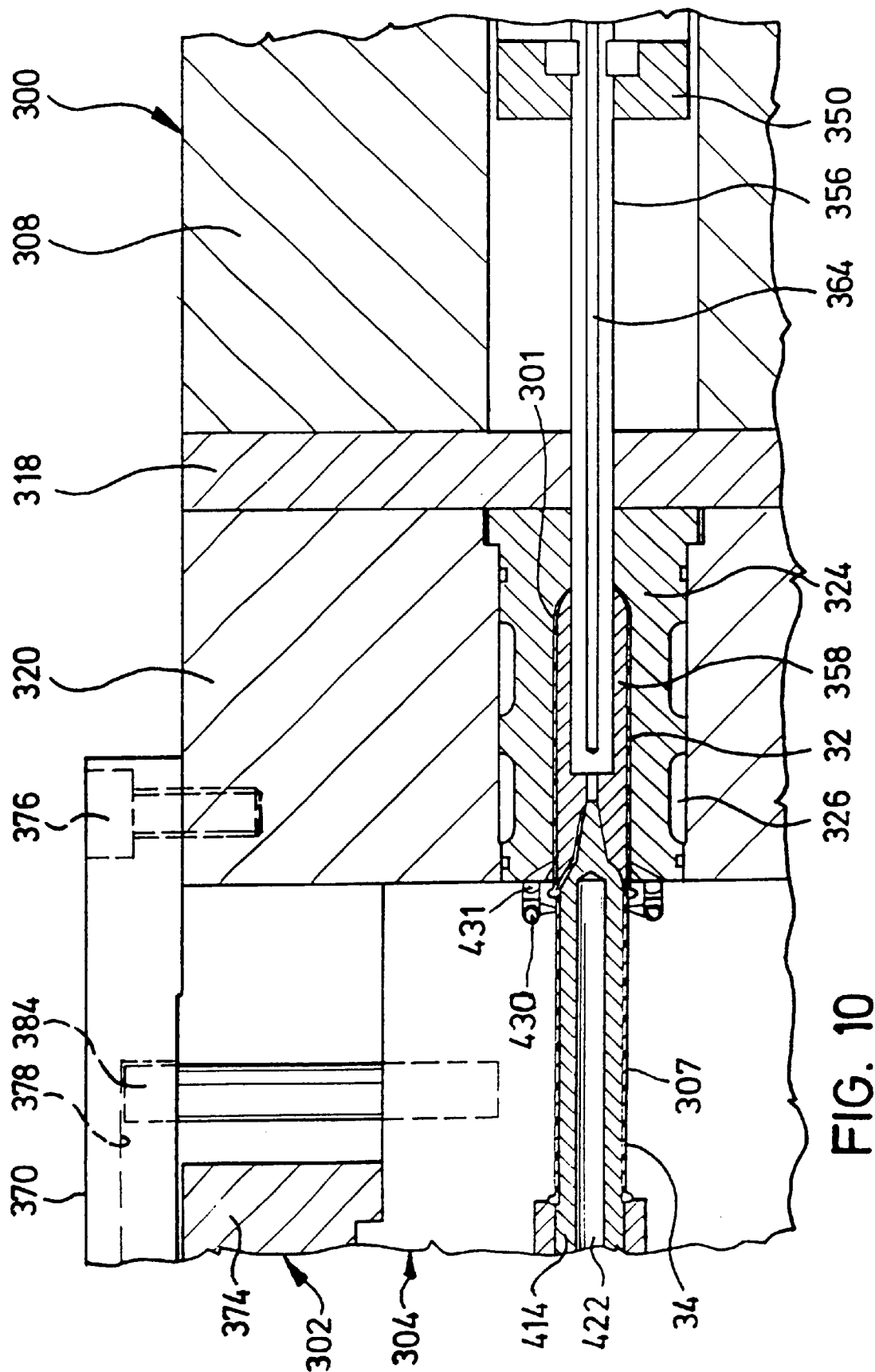
FIG. 10 shows the closed mold for the first embodiment of the one-part applicator molding according to FIGS. 1 to 4 on an enlarged scale.
Figure 11:
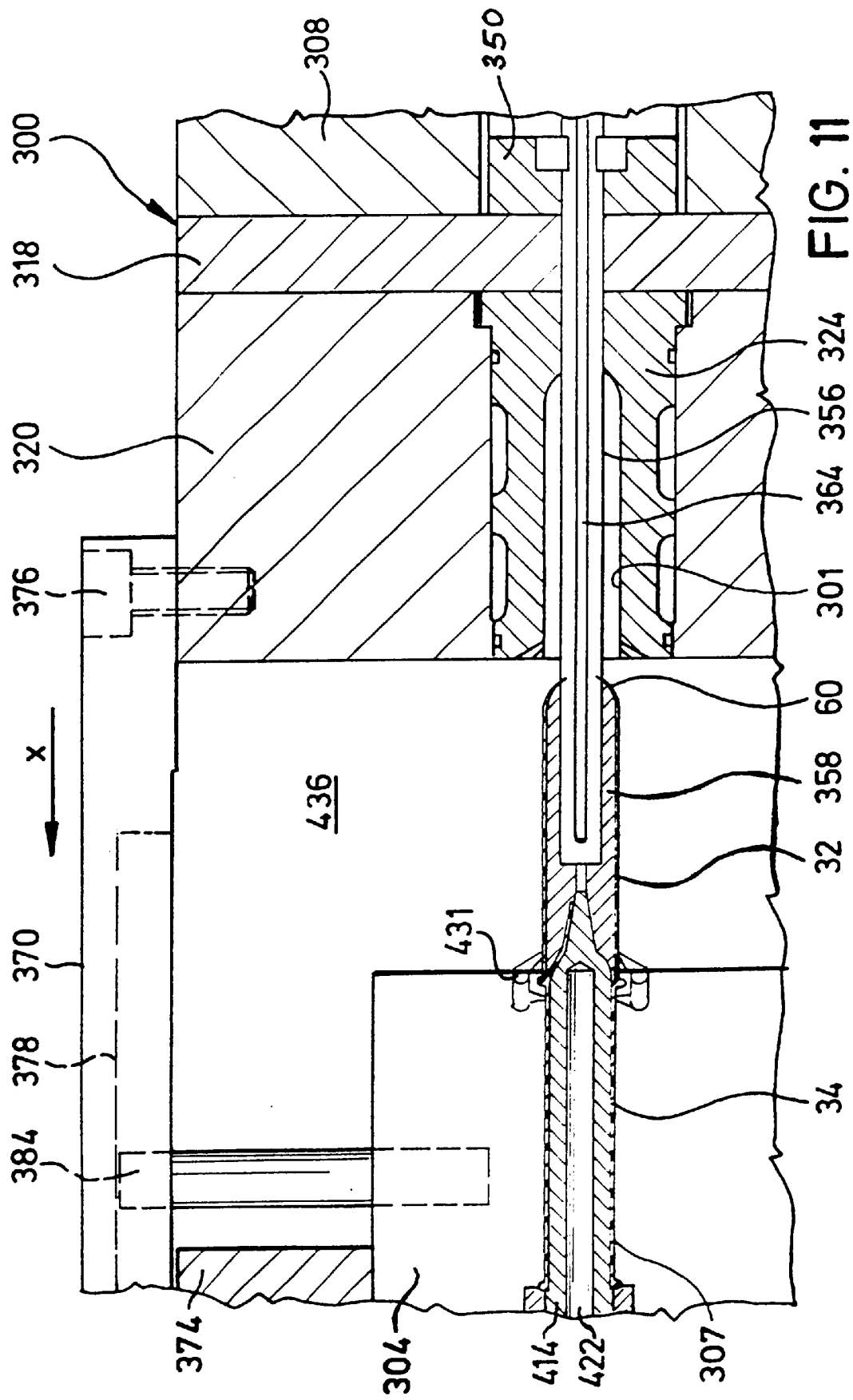
FIG. 11 shows a view similar to FIG. 10, in which the clamping unit for the applicator molding in FIGS. 1 to 4 assumes a first opening-stroke position.

In FIGS. 6, 7, 10 to 12, a cam plate 370, 372 is fastened by means of screws 376 in each case on the opposite longitudinal sides, parallel to the principle axes of the molds EP; U.S., of the sprue-side carrier plate 320 for the outer-sleeve mold inserts 324, 328 (FIGS. 7, 10 and 11). The cam plates 370, 372 are in each case provided on their inner side with a cam 378, 380. As FIGS. 6 and 7 show, the cams 378, 380 extend parallel to the direction of movement x of the clamping unit 302 and are cranked outward at their ends, facing away from the injection unit 300, with respect to the longitudinal center of the injection device over a section 382 (FIG. 6), which however is in turn directed parallel to the direction of movement x of the clamping unit 302 and is open at the end.

Figure 12:
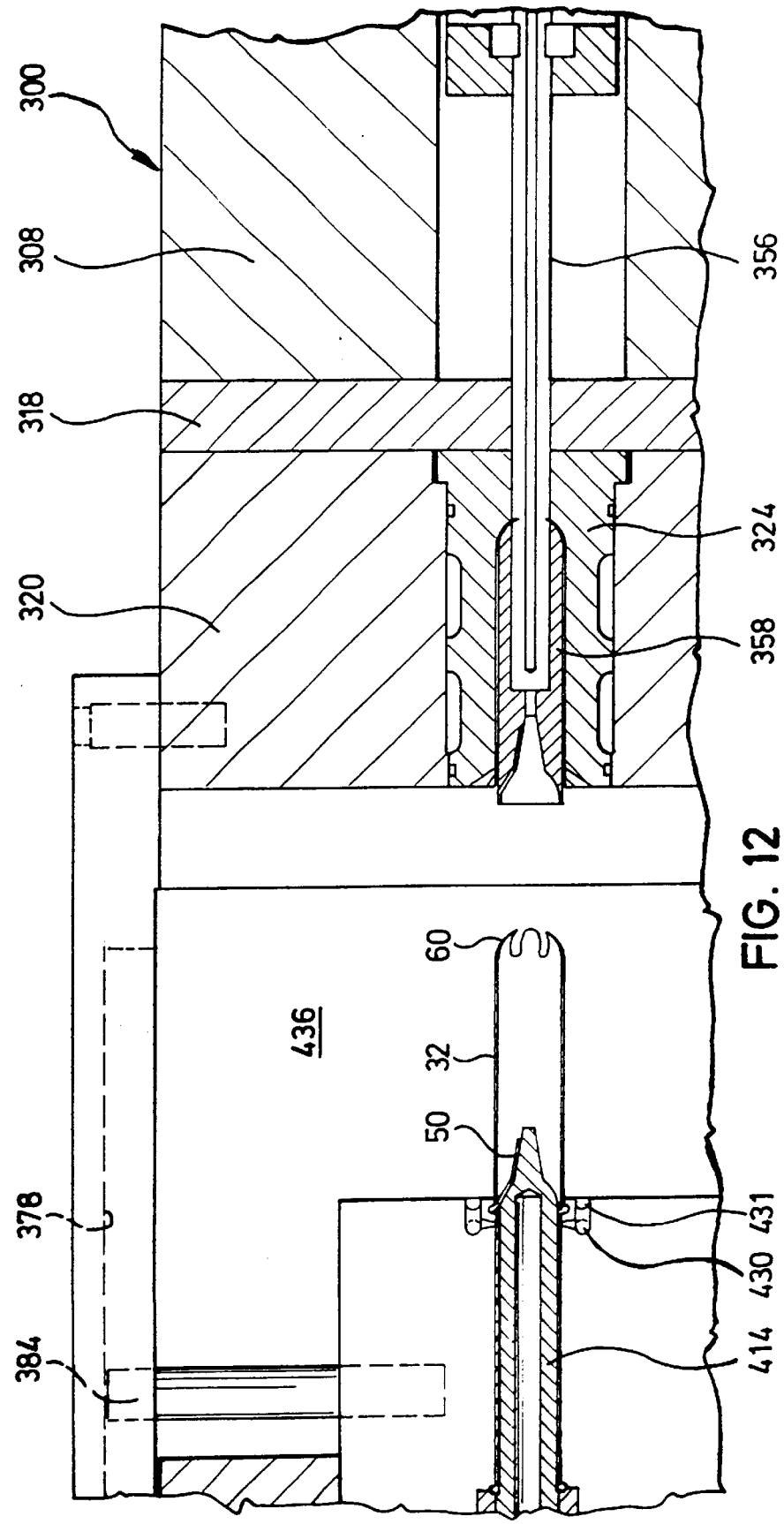
FIG. 12 shows a view similar to FIG. 11, with the clamping unit in a second opening-stroke position, the core of the outer sleeve having assumed its initial position again.

According to FIG. 7, the inner end of two control bolts 384, 386 is fastened on one of each of the two inner-sleeve mold jaws 388, 390 of the mold 304 represented in FIG. 6 or 8. The control bolts 384, 386 engage movably by their outer ends in the cams 378, 380. If the control bolts 384, 386 are located in the cranked section 382 of the cams 378, 380, the normally closed inner-sleeve mold 304 is open (FIGS. 11 and 12).

The clamping unit 302 has a platen 311 which, as FIG. 6 shows, is provided with bores 396, by which the clamping unit 302 can be connected through a mold clamping mechanism to a mold clamping drive, as known per se and therefore not represented. According to FIG. 7, the platen 311 and the fastening plate 412 have a central bore 402, through which a coupling rod 404 extends. The front end of the coupling rod 404 is firmly connected by means of a coupling screw 406 to the platen 407 and to the stripper plate 408, which is consequently movable back and forth in the direction of the machine via the coupling rod 404 connected to a preferably oil-hydraulic drive.

According to FIGS. 6 and 7, there extends between the platen 311 of the clamping unit 302 and a guide plate 375 a spacer frame 398, which keeps a space 399 free, in which the guide plate 375 is arranged movably back and forth parallel to itself. According to FIGS. 6, 7 and 10, the guide plate 375 bears on its side facing the injection unit 300 the mold 304 for the inner sleeves 34, 234, which is fastened by a fastening plate 374 onto the guide plate 375 by screws 377.

According to FIGS. 6 and 8, the two inner-sleeve mold jaws 388, 390 of the mold 304 are guided on oblique guide bolts 392, 393, which are fastened in the sprue-side support plate 320 and form with the central longitudinal axis of the injection device an acute angle which opens in the direction of the clamping unit 302. Consequently, the inner-sleeve mold jaws 388, 390 can be displaced laterally out of the closed position, shown in FIGS. 6 and 7, into an open position when the control bolts 384, 386 enter into the outwardly cranked section 382 of the cams 378, 380 during the opening stroke of the clamping unit 302, and vice versa. The inner-sleeve mold jaws 388, 390 are equipped with bores 394 for coolant fluid.

According to FIGS. 6 and 7, the platen 311 of the clamping unit 302 is firmly connected on its side facing the injection unit 300 by anchoring screws 400 to a fastening plate 412, in which cores 414 and 418 for the inner sleeves 34 and 234, respectively, are fastened. The substantially cylindrical inner-sleeve cores 414, 418 extend forward into a spherical-segmental part, in which there are axially forward and radially convex mold cavities 458 (FIG. 8) for forming the lips 48 of the inner sleeve 34. From the spherical-segmental part, the inner sleeves 34 or 234 extend with front, conically tapering centering tips 446 and 447 into approximately correspondingly shaped, conical openings of the outer-sleeve cores 358 and 360, respectively, when the mold is closed, as FIG. 7 shows. In FIG. 8, only one of these openings is denoted by 442. The inner-sleeve cores 414, 418 are provided with coolant channels 422, 424, which are connected to the coolant source (not shown). Furthermore, guide rods, of which only one is denoted by 410, are fastened in the fastening plate 412 axially parallel to the principle axis of the mold.

According to FIGS. 6 and 7, arranged in front of the fastening plate 412 is a platen 407, on which a stripper plate 408 is fastened by means of countersunk screws 409.

In the stripper plate 408 there are fastened two stripping sleeves 426; 428, which are in each case displaceably mounted coaxially on one of the two inner-sleeve cores 414, 418 and extend through the guide plate 375 into the inner-sleeve mold 304. FIG. 7 also shows that both the platen 407 and the stripper plate 408 are guided movably by guide sleeves 415 on the guide rods 410.

Figure 9:
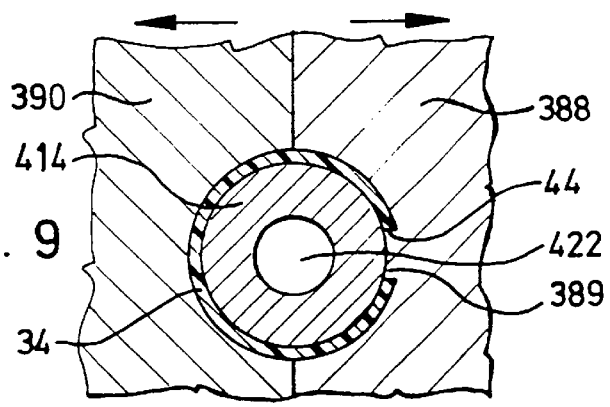
FIG. 9 shows a cross section IX—IX of the mold for the inner sleeve in FIG. 8, in a view turned through 90° about the principal axis of the mold.

FIGS. 8 and 9 show that the inner-sleeve mold jaw 388 is provided with a mold strip 389 for the guide slot 44 of the inner sleeve 34. In the closed position of the mold 304 shown in FIGS. 8 and 9, the mold strip 389 rests right on the inner-sleeve core 414, so that the guide slot 44 is left during the injection molding of the inner sleeve 34. The mold jaw 388 is also provided with a further mold strip, not shown however, for producing the longitudinal slot 244 in the inner sleeve 234 of the applicator molding 230 in FIG. 5.

According to FIG. 8, above and below the mold cavities 301, 307 formed by the inner-sleeve mold jaws 388, 390 of the mold 304 there are provided in the region of a mold parting plane 306 between the injection unit 300 and the clamping unit 302 runners 430, 431 and injection channels 456 as well as a bead cavity 452 for the outer sleeve 32 and a bead cavity 453 for the gripping bead 68 of the inner sleeve 34. The runners 430, 431 are separated by a separating wall 433. Consequently, moldable materials of different consistencies and/or colors can be injected through these two runners 430, 431 into the mold cavities 301, 303, 307, 309, in order to produce both the outer sleeves 32, 232 and, in connection with the latter, the inner sleeves 34, 234 of the one-part applicator moldings 30, 230 simultaneously, as is evident from the closed injection position of the molds EP and U.S. in FIG. 7. If need be, the separating wall 433 may also be omitted, if only one moldable material is to be injected into the mold cavities through the runners 430, 431. Under certain circumstances, however, it is also conceivable, in spite of the omission of the separating wall 433, to inject one moldable material of a quite particular nature, for example consistency and/or color, through the runners 430 and at the same time a moldable material of a different nature, for example consistency and/or color, than the first-mentioned, moldable material through the other runners 431 into the mold cavity 301, 307 and 303, 309.

FIG. 8 shows the mold 304 for the first embodiment of the applicator molding 30 according to FIG. 4 on an enlarged scale. It is clearly evident that the conical opening 442 in the front end of the outer-sleeve core 358 in the mold insert 324 is connected to the coolant channel 364 in the outer-sleeve core 358 by a coaxial connection channel 444. In the injection position of the inner-sleeve mold 304 according to FIG. 8, this connection channel 444 is closed by the conical centering tip 446 of the inner-sleeve core 414.

In FIG. 8 there can be seen a lateral cavity 448 for forming the tampon catch 50 in the wall of the conical opening 442 of the outer-sleeve core 358. The cavity 448 is in connection with the mold cavities 301 and 307 for the outer sleeve 32 and the inner sleeve 34, so that the unified production of the tampon catch 50 on the inner side of the wall 52 of the outer sleeve 32 together with the inner sleeve 34 is possible (FIGS. 1 to 3). For this purpose, there open into the mold cavity 301 of the mold insert 324 the conically tapering injection channels 450 contained therein, which are connected to the runners 431 in the inner-sleeve mold jaws 388, 390 when the mold is closed. The runners 430 open into the radial injection channels 456, which are in connection with the mold cavity 307 for the inner sleeve 34 behind a bead cavity 452 for the gripping bead 70.

The amount of a single type of molding material, such as for example polyethylene or polypropylene, necessary for molding the one-part applicator molding 30 can be injected through the runners 430, 431. As mentioned the runners 430, 431 may, also be optionally connected to mutually separate molding material sources. In the latter case, if need be the molding materials used may be composed differently in terms of color and consistency, if it is desired to give priority to the special function of the outer sleeve 32 with the tampon catch 50 or of the inner sleeve 34 of a tampon applicator. In this case, the molding materials of different compositions and/or colors may be injected simultaneously or just with a slight time difference into the molds 304 and into the mold inserts 324 or 328. In this case the mixing of the two molding materials occurring in the injection region is slight and therefore can be disregarded.

FIG. 10 shows an enlarged view of the mold EP, where the mold cavities 307, 309 of the mold 304 for the inner sleeves 34, 234 and the mold cavities 301, 303 for the outer sleeves 32, 232 in the mold inserts 324, 328 of the support plate 320 form a common mold cavity for the one-part applicator molding 30; 230.

Figure 13:
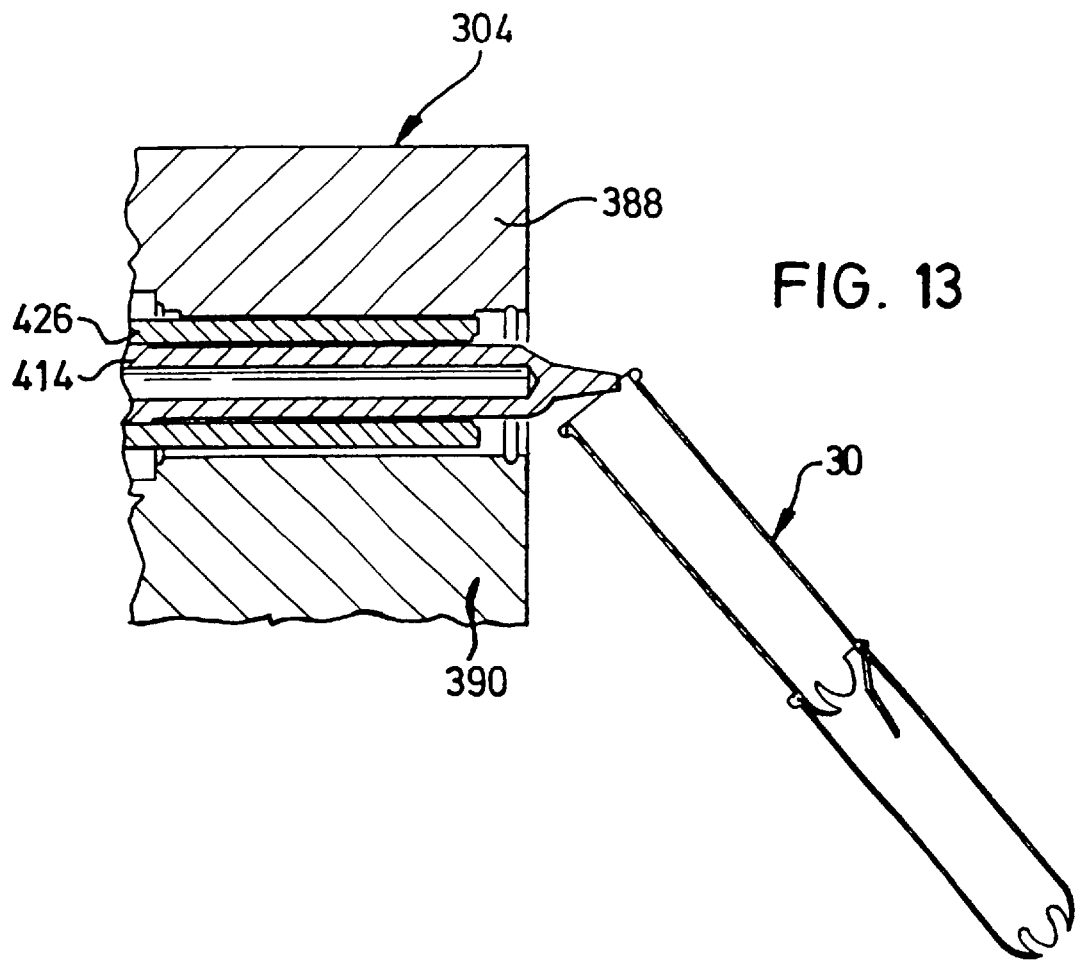
FIG. 13 shows a third opening-stroke position of the clamping unit, in which the opened inner-sleeve mold with a stripping sleeve in its stripping-stroke end position and ejected applicator molding can be seen in a central longitudinal section in an enlarged, partially broken-away representation.

In FIGS. 11, 12 and 13, three successive opening stroke positions of the clamping unit 302 are represented, for the sake of clearer representation on an enlarged scale, only by the most important component parts of the mold EP for the one-part applicator molding 30 in FIG. 4, because the mold U.S. functions correspondingly.

In FIG. 11, the clamping unit 302 has been moved on a first opening stroke into a first opening position after the molding of a one-part applicator molding and its brief curing with the inner-sleeve mold 304. The two control bolts 384, 386 for the mold jaws 388, 390 of the inner-sleeve mold 304 are in this case located in a position which lies approximately midway along the cams 378, 380. With the opening movement of the clamping unit 302, the piston-cylinder units 340, 342 are actuated such that, according to FIG. 11, the profile core 356 fastened on the supporting plate 350, with its outer-sleeve core 358 bearing right against the conical centering tip 446 of the inner-sleeve core 414, is moved out from the corresponding mold insert 324 at synchronous speed in the opening direction of the clamping unit 302. The inner-sleeve core 414 consequently continues to engage in a sealing manner by its conical centering tip 446 in the conical centering opening 442 of the inner core 358 for the outer sleeve 32. Alternately, shown in FIG. 11 are merely the runners 431, through which the moldable material is injected into the mold cavities 301, 307; 303; 309.

In FIG. 12, the apparatus is represented in a second open-stroke position. This position is characterized by two preceding movement operations: by the movement of the supporting plate 350 by means of the piston-cylinder units 340, 342 in the direction of the injection unit 300, the core 358 has been completely moved back out of the outer sleeve 32, surrounding it, of the one-part applicator molding into the mold insert 324. During this return travel of the outer-sleeve inner core 358, the lips 60 at the front end of the outer sleeve 32, now projecting freely into an interspace 436 between the injection unit 300 and the clamping unit 302, have been spread; however, on account of the resilience typical for molding material, such as plastic, or the so-called memory effect, the lips 60 resume their round dome-like shape once the core 358 has been completely moved out from the outer sleeve 32. The control bolts 384, 386 have now assumed a first end position, lying in opening direction x, of their rectilinear movement in the cams 378, 380 of the cam plates 370, 372, such that the inner-sleeve mold jaws 388, 390 are still closed.

Figure 14:
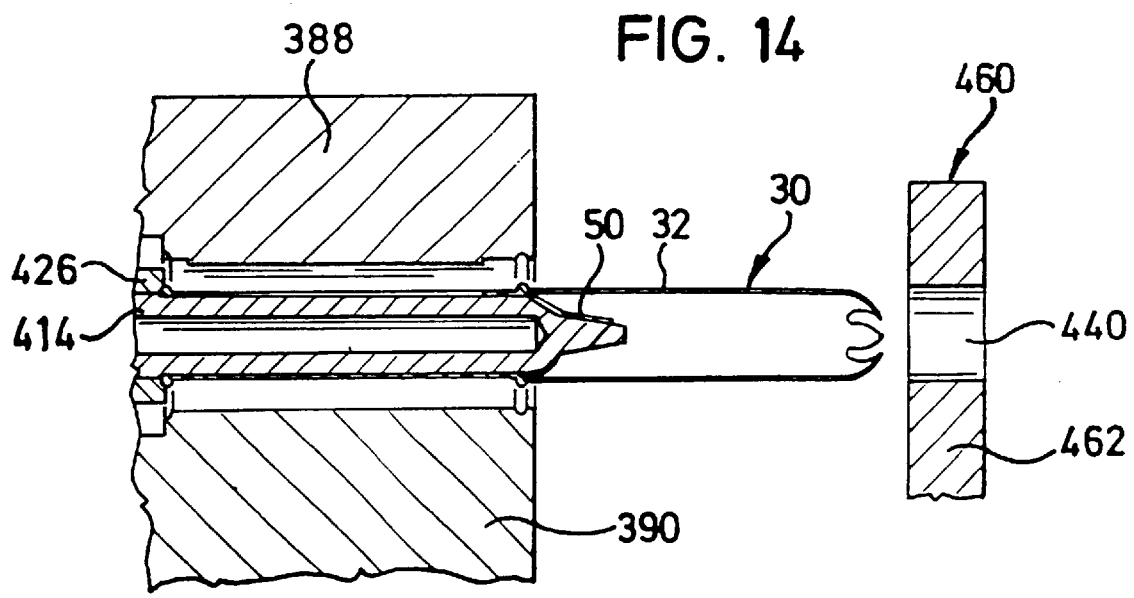
FIG. 14 shows a view similar to FIG. 13, with opened inner-sleeve mold and the applicator molding and also a handling device for the assembly of the applicator in an injection-molding machine.

With reference to FIGS. 6, 10 and 13, the operation of the mold for the production of the one-part applicator molding can now be ended by the clamping unit 302 in FIGS. 6 and 7 being moved further in the direction of the arrow x into a third opening position by actuation of the hydraulic cylinder-piston units 340, 342. The control bolts 384, 386 of the inner-sleeve mold 304 thereby slide into a second, final end position in the outwardly cranked section 382 of the cam plates 370, 372 and thereby move the inner-sleeve mold jaws 388, 390 into an open position, which is shown in FIG. 14. Thereafter, as FIG. 14 shows, the movable stripper plate 408 with the stripping sleeve 426 has been moved in the direction of the injection unit 300 and the one-part applicator molding 30 has been ejected from the inner-sleeve mold 304. At the same time, the front end face of the stripping sleeve 426, moved in the direction of the injection unit 300, has acted on the rear end face of the gripping bead 68 of the inner sleeve 34 seated on its inner core 414, which inner sleeve, as described, is connected by the molded-on predetermined breaking points 36 to the outer sleeve 32 of the one-piece applicator molding 30. Subsequently, the one-part applicator molding 30 can be fed to further work stations (not shown) and a new molding cycle can be initiated.

Figure 15:
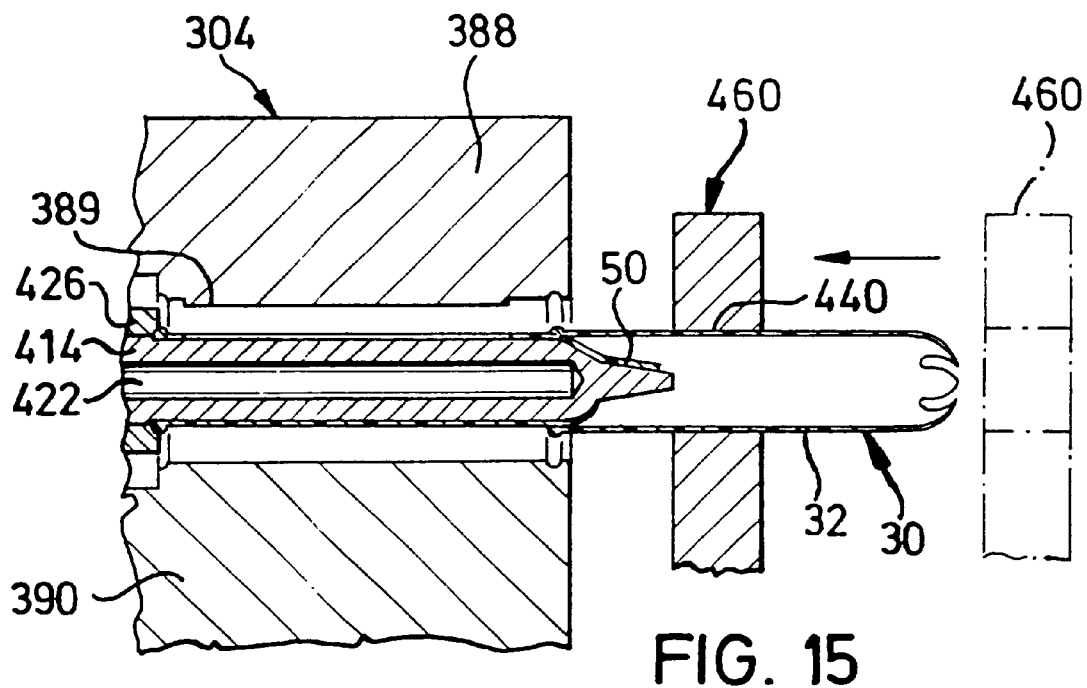
FIG. 15 shows a view similar to FIG. 14, with the opened inner-sleeve mold and the applicator molding, the outer sleeve being seized by the handling device.

The invention permits, however, not only the one-part production of the applicator molding 30 or 230, but in addition also a finished assembly of the tampon applicator within the injection-molding machine. These further process steps are explained below with reference to FIGS. 14 to 16.

FIG. 14 corresponds to the end position, shown in FIG. 12, of the opening stroke of the clamping unit 302, in which there is the interspace 436 between the injection unit 300 and the clamping unit 302. As a result, according to FIG. 12, this interspace 436 between the injection unit 300 and the clamping unit 302 is large enough that a handling device 460, shown in FIG. 14, can be actuated, which device is movable both perpendicular and parallel to the principle axis of the mold. Consequently, the handling device 460 according to FIG. 14 can be moved into the interspace 436 between the injection unit 300 and the opened clamping unit 302 and, according to FIG. 15, by a subsequent movement coaxial to the inner-sleeve mold 304, can receive the outer sleeve 32 of the one-part applicator molding 30 in a receiving bore 440, the diameter of which is adapted to the outside diameter of the outer sleeve 32.

Figure 16:
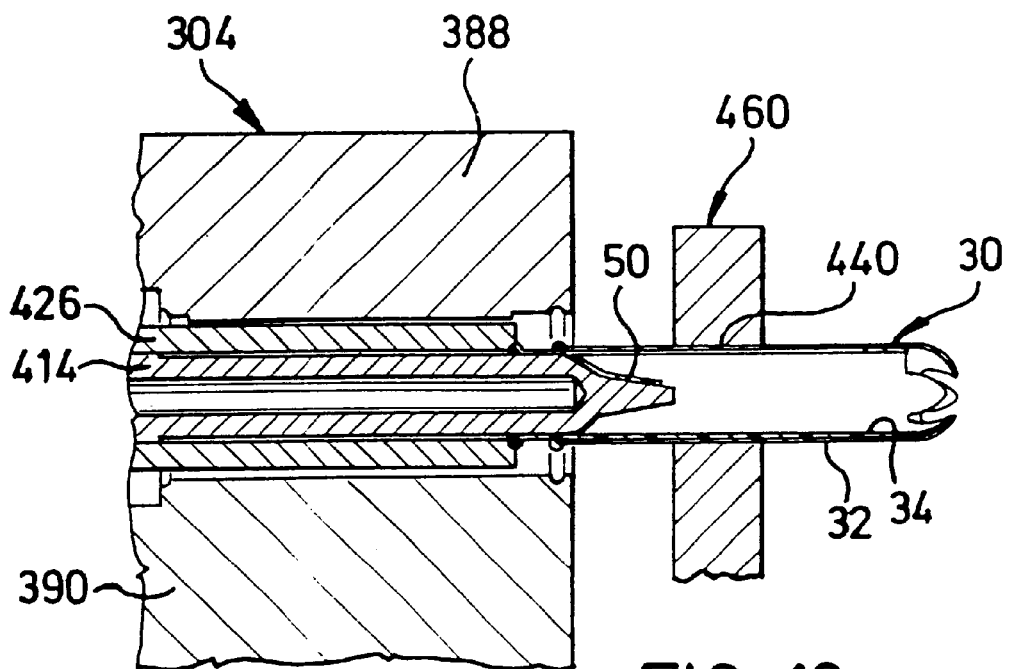
FIG. 16 shows a view similar to FIG. 15, which represents the assembly of the tampon applicator by means of the handling device.

Thereafter, according to FIG. 16, the movable stripper plate 408, shown in FIG. 7, of the clamping unit 302 is advanced in the direction of the injection unit 300, with the result that the front end of the stripping sleeve 426 takes up the rearward end of the inner sleeve 34 and, destroying the predetermined breaking points 36 between inner sleeve 34 and outer sleeve 32 of the applicator molding 30, pushes the inner sleeve 34 into the outer sleeve 32, which at the same time is introduced completely into the receiving bore 440 of the handling device 460. When the predetermined breaking points 36 (FIG. 3) are destroyed, the said hook-shaped attachments are produced on the inner side of the outer sleeve 32 or 232 and also on the outer side of the inner sleeve 34 or 234. When the inner sleeve 34 is pushed into the outer sleeve 32, the attachments on the inner side of the bead 70 of the outer sleeve 32 engage in a detaining manner as catching hooks in the annular catching groove 71 at the rear end of the inner sleeve 34 (FIG. 4).

When the inner sleeve 234 is pushed into the outer sleeve 232 in FIG. 5, the catching hooks caused by the destruction of the predetermined breaking points 36 are moved over the annular catching bead 72 and come to bear in a detaining manner against the circumferential surface of the inner sleeve 234, which extends between the catching bead 72 and the gripping bead 268. It goes without saying that the inner sleeve 34 in FIG. 4 could also be provided with a catching bead and the inner sleeve 234 in FIG. 5 could also be provided with a catching groove. In addition, correspondingly acting catching means could also be provided only on parts of the circumference which lie in the direction of alignment of the catching hooks originating from the destroyed predetermined breaking points.

The detention described above of the inner sleeve 34 or 234 pushed into the outer sleeve 32 or 232 ensures that this pushed-in position of the inner sleeve in the outer sleeve is retained during the further handling of the tampon applicator, for example during insertion of the tampon into the inner sleeve and the packing of the tampon applicator. At the same time, however, it is ensured that putting the tampon applicator to use, initially by withdrawing the inner sleeve 34 or 234 from the corresponding outer sleeve 32 or 232, is not hindered, because the detaining connection can be easily overcome by virtue of the flexibility of the sleeves.

When the inner sleeve 34 is pushed into the outer sleeve 32, the spring leaf-like tampon catch 50 is initially bent by the front end of the inner sleeve 34 against the flexibly compliant wall 52 of the outer sleeve 32, before it subsequently springs back into the guide slot 44 of the inner sleeve 34 and locks the latter axially movably with the outer sleeve 32. This concludes the production and assembly of the tampon applicators.

To sum up, therefore, the process according to the invention for producing a tampon applicator from plastic for feminine hygiene can be broadly described by the following process steps:

In the closed state of the apparatus, moldable material is first of all injected from at least one runner 430; 431 approximately simultaneously into the mold cavities 301, 303 of the injection unit 300 for the outer sleeves 32; 232 and into the mold cavities 307, 309 of the clamping unit 302 for the inner sleeves 34; 234 of the molds EP; U.S., forming at least one predetermined breaking point 36 between the rear end of the outer sleeves 32; 232 and the front end of the inner sleeves 34; 234. Thereafter, the one-part applicator molding 30; 230 is allowed to cure to a certain temperature in the mold cavities 307; 309 for the inner sleeve 34; 234. The outer sleeves 32; 232 of the one-part applicator molding 30; 230 are then demolded, the outer sleeves 32; 232 surrounding their core 358, 360. The outer sleeves 32; 232 of the one-part applicator molding or blank 30; 230 are subsequently freed from their cores 358; 360, in that the cores 358; 360 of the outer sleeves 32; 232 are withdrawn through their front openings 62 or 262. The one-part applicator moldings 30; 230 are then ejected from the inner-sleeve mold cavities 307; 309 of the clamping unit 302 by stripping off their inner sleeves 34; 234 from the inner sleeve cores 358; 360, which are arranged within the inner sleeve mold cavities 307; 309 of the clamping unit 302.

During the injection operation, spherical-segmental lips 60; 260 are respectively formed on at the front end of the outer sleeves 32; 232 and of the inner sleeves 34; 234. When the cores 358; 360 are withdrawn from the outer sleeves 32; 232 of the all-in-one applicator moldings 30; 230, the spherical-segmental lips 60; 260 of the outer sleeves 32; 232 are temporarily spread by the outer-sleeve cores 358; 360 and subsequently again form a convex front end of the outer sleeves 32; 232. Furthermore, during the injection operation, a flexible, tongue-shaped tampon catch 50 is formed on the inner side of the wall 52 of the outer sleeves 32; 232 and at the same time there is formed in the wall of the inner sleeves 34; 234 an in each case different guide slot 44; 244, which is arranged coaxially with respect to the tampon catch 50. In addition, after the withdrawal of the outer-sleeve cores 358; 360, the outer sleeves 32; 232, protruding freely into the interspace 436 of the opened mold EP; U.S., of the one-part applicator moldings 30; 230 are seized around their circumference, and the inner sleeves 34; 234 are pushed by their cores 414; 418 in the injection unit 300 into the outer sleeves 32; 232, which are held substantially undisplaceably in the axial direction. At the same time, the at least one predetermined breaking point 36 between the outer sleeves 32; 232 and the inner sleeves 34; 234 of the applicator moldings 30; 230 is thereby destroyed. When the inner sleeves 34; 234 are pushed into the outer sleeves 32; 232, initially the leaf spring-like tampon catches 50 are bent by the flexible lip roots 46 of the inner sleeves 34; 234 against the inner side of the wall 52 of the outer sleeves 32; 232. Subsequently, the tampon catches 50 engage in the associated guide slots 44; 244, which in the wall of the inner sleeves 34; 234 are aligned coaxially with respect to their corresponding tampon catch 50 and are closed at both ends.

An advantage of the apparatus described above is that the inner sleeves 34, 234 are located in the inner-sleeve mold 304 of the clamping unit 302. This arrangement makes it possible to provide the outer surface of the inner sleeves 34, 234 with inscriptions, for example with an instruction for use for the handling of the tampon applicator. Such an instruction for use could be, for example, a directional arrow and the inscription "PULL". Once the inner sleeves 34, 234 have been pulled out from their outer sleeves 32, 232, there can be provided, for example, on the surface then exposed of the inner sleeves 34; 234 an arrow which points in the opposite direction and is provided with the inscription "PUSH".

The invention thus makes it possible to mold through the injection channels both the outer sleeves and the inner sleeves of the tampon applicators axially congruent in one and the same mold in a single molding operation and, by particular mold-opening strokes and ejecting strokes, to assemble the one-part tampon applicators in the injection-molding machine, i.e. to push the inner sleeves into the outer sleeves of the applicator moldings, destroying the predetermined breaking points, in exact, coaxial alignment with respect to one another, in such a way that the tampon catch 50 on the inner side of the outer sleeves 32; 232 engages in the associated longitudinal slot 44; 244 of the inner sleeves 34; 234 and the outer sleeves are interlocked to a certain extent with the associated inner sleeve. The handling device 460 may comprise a spreading rest or perforated plate 462, which enters the device, encloses the gripping beads 70; 270 of the outer sleeves 32; 232 and moves the tampon applicators out of the mold cavities and feeds them to a further processing station, while the mold can begin a new production cycle.

We claim:

1. Process for producing a tampon applicator for feminine hygiene from moldable material, the tampon applicator having an outer sleeve and an inner sleeve, the process comprising the steps of:

a) injecting the moldable material from at least one runner substantially simultaneously into a mold cavity for the outer sleeve formed between an outer sleeve mold and an outer sleeve core in an injection unit and into a mold cavity for the inner sleeve formed between an inner sleeve mold and an inner sleeve core of a clamping unit of a mold, the mold cavities being connected by at least one relatively thin runner to form at least one predetermined breaking point between the rear end of the outer sleeve and the front end of the inner sleeve of a one-part applicator molding;

b) solidifying the one-part applicator molding in the mold cavities;

c) removing the outer sleeve mold from the outer sleeve of the one-part applicator molding;

d) coaxially withdrawing the outer sleeve core through a front opening of the outer sleeve of the one-part applicator molding;

e) ejecting the one-part applicator molding from the inner-sleeve mold cavity.

2. The process of claim 1 which further comprises the step of forming a flexible, tongue-shaped tampon catch on an inner surface of the outer sleeve proximate a rear end, opposite the front end thereof, and a longitudinal guide slot in the inner sleeve which is arranged coaxially with respect to the tampon catch.

3. Process for producing a tampon applicator for feminine hygiene from moldable material, the tampon applicator having an outer sleeve and an inner sleeve, the process comprising the steps of:

a) injecting the moldable material from at least one runner substantially simultaneously into a mold cavity for the outer sleeve formed between an outer sleeve mold and an outer sleeve core in an injection unit and into a mold cavity for the inner sleeve formed between an inner sleeve mold and an inner sleeve core of a clamping unit of a mold, forming segmented, curved lips at the front end of the outer and inner sleeves, the mold cavities being connected by at least one relatively thin runner to form at least one predetermined breaking point between the rear end of the outer sleeve and the front end of the inner sleeve of a one-part applicator molding;

b) solidifying the one-part applicator molding in the mold cavities;

c) removing the outer sleeve mold from the outer sleeve from the one-part applicator molding;

d) coaxially withdrawing the outer sleeve core through a front opening of the outer sleeve of the one-part applicator molding; and e) ejecting the one-part applicator molding from the inner-sleeve mold cavity.

4. The process of claim 3 which further comprises the step of moving the inner sleeve axially into the outer sleeve to destroy the at least one predetermined breaking point.

5. The process of claim 4 wherein the outer sleeve is substantially immobilized while the inner sleeve is moved into the outer sleeve by movement of the inner sleeve core.

6. The process of claim 5 wherein the tampon catch and the front end of the inner sleeve deform during the relative movement of the sleeves to permit the tampon catch to be displaced into the inner sleeve guide slot.

7. Process for producing a tampon applicator for feminine hygiene from moldable material, which applicator comprises an approximately cylindrical outer sleeve and an approximately cylindrical inner sleeve, the outside diameter of which is made smaller than the inside diameter of the outer sleeve and which can be arranged telescopically displaceably in the outer sleeve, the process comprising the injection of moldable material into a mold cavity with an inner core for the outer sleeve and into a mold cavity with an inner core for the inner sleeve of the tampon applicator, involving the following process steps:

a) the moldable material is injected from at least one runner approximately simultaneously into the mold cavity for the outer sleeve in an injection unit and into the mold cavity for the inner sleeve of a clamping unit of a mold, forming at least one predetermined breaking point between the rear end of the outer sleeve and the front end of the inner sleeve of a one-part applicator molding;

b) the one-part applicator molding is allowed to cure to a certain temperature in the mold cavities;

c) the outer sleeve of the one-part applicator molding is demolded, the outer sleeve surrounding its core;

d) the outer sleeve of the one-part applicator molding is freed from its core, in that the core of the outer sleeve is coaxially withdrawn through the front opening of the latter;

e) the one-part applicator molding is ejected from the inner-sleeve mold cavity of the movable, opened clamping unit by stripping off its inner sleeve from the core of the latter, which is arranged within the inner-sleeve mold cavity of the clamping unit.

8. An apparatus for producing a tampon applicator for feminine hygiene from moldable material, the apparatus comprising an injection unit and a clamping unit, that together in a closed state meet to form a parting plane and form an outer sleeve mold cavity having an outer sleeve core that is arranged in the injection unit and an inner sleeve mold cavity having an inner sleeve core that is arranged in the clamping unit, wherein at least one runner connects the outer and inner sleeve mold cavities in the region of the parting plane to produce at least one predetermined breaking point between a rear end of the outer sleeve and a front end of the inner sleeve of the one-part applicator molding.

9. The apparatus of claim 8, wherein outer sleeve mold cavity is provided with a longitudinal bore, in which an axially movable, longitudinally extending profile core is mounted, a distal end of which forms the outer sleeve core.

10. The apparatus of claim 8, wherein an axial, conical opening having an axial depression for molding a tampon catch extending inwardly from a rear end of the outer sleeve is provided in a front end of the inner sleeve core.

11. The apparatus of claim 8, wherein the inner sleeve mold cavity is arranged on the clamping unit facing the injection unit and the inner sleeve mold cavity is movable radially and synchronously with respect to the inner sleeve core.

12. The apparatus of claim 8, wherein the inner sleeve mold cavity is provided with a guide-slot mold strip, which in the closed state of the inner-sleeve mold bears against the inner sleeve core to form a guide slot in the inner sleeve.

13. The apparatus of claim 8, wherein the inner sleeve mold cavity is operatively connected runners that extend around the opening of the inner sleeve mold cavity at the parting plane, and in the closed position of the mold, are in connection with the outer sleeve mold cavity via conically tapering injection channels.

14. The apparatus of claim 8, wherein the rear end of the inner sleeve core is rigidly fastened on a fastening plate of the clamping unit and extends through a stripping sleeve.

15. The apparatus of claim 14, wherein the front end of the inner sleeve core has a conical centering tip to coaxially center the inner sleeve core in the outer sleeve core.

16. An apparatus for producing a tampon applicator for feminine hygiene from moldable material, the apparatus comprising an injection unit and a clamping unit, that together in a closed state meet to form a parting plane and form an outer sleeve mold cavity having an outer sleeve core that is arranged in the injection unit, wherein outer sleeve mold cavity is provided with a longitudinal bore, in which an axially movable, longitudinally extending profile core is mounted, a distal end of which forms the outer sleeve core, wherein a proximal end of the profile core is fastened on a supporting plate that is mounted movably back and forth in the injection unit by means of a drive mechanism, and an is inner sleeve mold cavity having an inner sleeve core that is arranged in the clamping unit, wherein at least one runner connects the outer and inner sleeve mold cavities in the region of the parting plane to produce at least one predetermined breaking point between a rear end of the outer sleeve and a front end of the inner sleeve of the one-part applicator molding.

17. The apparatus of claim 16, wherein the drive mechanism comprises at least one piston-cylinder unit fastened on a fixed receiving plate and connected to the supporting plate.

18. The apparatus of claim 16, wherein the outer sleeve core has a convex end face and recesses for molding lips at the end of the outer sleeve to which the profile core is attached.

19. The apparatus of claim 16, wherein a handling device is provided for securing the outer sleeve of the one-part applicator molding while the inner sleeve is stripped off from the inner sleeve core to cause the at least one predetermined breaking point to be destroyed, pushing the inner sleeve to a locked position by engaging at least one catching hook, formed on the outer sleeve by the destruction of the predetermined breaking point, with a catching element formed on the inner sleeve.

20. The apparatus of claim 19, wherein the handling device comprises a perforated plate that is provided with receiving through-bores for at least one outer sleeve.

21. An apparatus for producing a tampon applicator for feminine hygiene from moldable material, the apparatus comprising an injection unit and a clamping unit, which in a closed state form a mold cavity with inner core, wherein the mold cavity with a core for the outer sleeve is arranged in the injection unit and the mold cavity with a core for the inner sleeve is arranged in the clamping unit of the apparatus and, in the closed state of the mold, form a single mold cavity for a one-part applicator molding, there being provided in the closed molding position of the mold, in the region of its parting plane, at least one runner between the mold cavities for producing at least one predetermined breaking point between the rearward end of the outer sleeve and the front end of the inner sleeve and the front end of the inner sleeve of the one-part applicator molding.

* * * * *